United States Patent [19]

Russel, Jr. et al.

[11] Patent Number: 4,745,907
[45] Date of Patent: May 24, 1988

[54] SYSTEM AND METHOD FOR DELIVERING INSOLUBLE MATERIALS INTO A LIVING BODY

[75] Inventors: John L. Russel, Jr., Alpharetta; John L. Carden, Tucker, both of Ga.

[73] Assignee: Nuclear Medicine, Inc., Atlanta, Ga.

[21] Appl. No.: 98,744

[22] Filed: Sep. 16, 1987

Related U.S. Application Data

[63] Continuation of Ser. No. 761,736, Aug. 1, 1985, abandoned.

[51] Int. Cl.$^4$ .................. A61M 37/04; A61N 5/01
[52] U.S. Cl. ................... 128/1.1; 128/654; 604/57; 604/84; 604/85; 604/903
[58] Field of Search .............. 128/1.1, 1.2, 654, 655; 604/57, 82, 84, 85, 903

[56] References Cited

U.S. PATENT DOCUMENTS

| | | | |
|---|---|---|---|
| 1,170,805 | 2/1916 | Eastman | 604/12 K |
| 1,655,664 | 1/1928 | Russell | 604/85 |
| 3,498,136 | 3/1970 | Le May | 73/426 |
| 4,154,109 | 5/1979 | Kelson | 74/429 |
| 4,233,973 | 11/1980 | Shukla | 128/214 R |
| 4,424,056 | 1/1984 | Urquhart et al. | 606/56 |
| 4,465,471 | 8/1984 | Harris et al. | 604/56 |
| 4,562,829 | 1/1986 | Bergner | 128/1.1 |
| 4,585,009 | 4/1986 | Barker et al. | 128/655 |
| 4,623,334 | 11/1986 | Riddell | 64/85 |

OTHER PUBLICATIONS

Zielinski and Kasprzyk, "Synthesis and Quality Control Testing of $^{32}$P Labeled Ion Exchange Resin Microspheres for Radiation Therapy of Hepatic Neoplasms," Int. J. Appl. Radiat. Isot. 34, 1343–1350 (1983).

Primary Examiner—Kyle L. Howell
Assistant Examiner—John C. Hanley
Attorney, Agent, or Firm—Fitch, Even, Tabin & Flannery

[57] ABSTRACT

To deliver a controlled dosage of an insoluble material into a living body, the material is provided in measured amounts in vials, and a system is provided for flushing the entire content of insoluble materials from the vial into the body. Insoluble radioactive material, such as glass microspheres incorporating radioactive isotopes, are packaged in a plurality of vials, preferably with different amounts of material. An accurate dosage of radioactivity can be delivered by administering the entire contents of one or more vial(s) according to the sum of radioactivity in selected vials as determined by the initial measurement of radioactivity and by the natural half-life of the isotope.

8 Claims, 1 Drawing Sheet

SYSTEM AND METHOD FOR DELIVERING INSOLUBLE MATERIALS INTO A LIVING BODY

This application is a continuation of application Ser. No. 761,736 filed Aug. 1, 1985, now abandoned.

The present invention is directed to delivery of small insoluble material particles into the human body, and more particularly is directed to controlling the dosage of a difficult to handle insoluble material, such as radioactive microspheres, into a living body.

BACKGROUND OF THE INVENTION

The use of radiation as a means for selectively destroying malignant cells has been known for some time. In cases where the malignancy is localized, there are a number of advantages to localizing the administration of radiation to the site of malignancy. One means of locally administering dosages of radioactivity is to implant radioactive material into the body so that it resides at the site of the malignancy. Such material may be provided in the form of microspheres or pellets containing a radioactive isotope. This method has the further advantage in that radiation is continuously administered to the tissue.

It is known, for example, to provide microspheres, such as glass microspheres, that contain a radioactive isotope within the glass. Radioactive glass microspheres having diameters between about 15 and 50 microns are particularly useful in the treatment of malignant liver tumors. The microspheres are introduced along with a body-compatible carrier fluid into the hepatic artery, whereupon the microspheres travel to and lodge in capillaries of the liver and in liver tumors. The liver receives approximately 20% of its blood supply through the hepatic artery and the remaining 80% from the portal vein which leads from the digestive organs. Liver tumors, on the other hand, tend to draw their entire blood supply from the hepatic artery; thus, radioactive microspheres introduced into the hepatic artery selectively localize in capillaries associated with liver tumors.

In the past, radioactive microspheres have been simply injected into the bloodstream via a catheter, usually with a syringe having an awkward shield to protect the physician from radiation. In addition to shielding problems, many insoluble radioactive materials are difficult to administer in controlled dosages. The radioactive isotopes that are generally incorporated in radioactive microspheres or pellets for localized radiation treatment have short half-lives. Thus, there is a very significant, though entirely predictable, loss of radioactivity (decay) from the time the material is shipped from the place of manufacture until it is administered to a patient. The amount of material to be administered, therefore, is a function of the amount of measured radioactivity per mass of material and of the time interval between the date of measurement and the date of administration.

Heretofore, insoluble radioactive material has been provided in vials along with a volume of carrier liquid. The radioactivity of the material is measured at a certain time, which is dated on the vial, and the physician is provided tables relating desired dosage to date of use. Immediately prior to usage, the vial is shaken until the insoluble material is, presumably, homogeneously distributed throughout the carrier liquid, and an appropriate volume is withdrawn by syringe.

Delivery of a desired dosage by syringe withdrawal measurement rests upon the assumption that the insoluble material is homogeneously distributed throughout the carrier fluid; however, this is a very dubious assumption, especially with denser materials. Even attempts to maintain agitation, e.g., by continuous stirring, while withdrawing the insoluble material and carrier liquid, may not assure a withdrawal of insoluble particles that is proportional to the volume withdrawn. Glass microspheres typically have a density of about 3.1 $gm/cm^3$, whereas isotonic saline, or another suitable carrier salt solution, has a density only slightly greater than unity. Administration of a desired dosage of dense insoluble material based upon suspension volume is inherently unreliable.

Syringe injection introduces further uncertainties of dosage. For reasons, such as mechanical entrapment or electrostatic attraction of surfaces, a potentially significant portion of the insoluble radioactive material tends to remain in the syringe.

The need exists for systems and methods for delivering insoluble materials into an animal body, including a human body, with more precise control over dosage. Where the insoluble material is radioactive, the need exists for better shielding of the material from the physician.

SUMMARY OF THE INVENTION

In accordance with the present invention, insoluble material, such as radioactive glass microspheres, are provided in a set of vials, each containing a known quantity of the insoluble material. The quantity in each vial is a fraction of a total quantity in the plurality of vials of the set. A particular dosage that is desired can be provided by administering the entire content of one or more selected vials of known content, thereby eliminating the need to withdraw a fractional portion of the contents of any one vial. To deliver the entire contents of a selected number of vials, inlet means of the vials are simultaneously or successively communicated with a fluid source, and outlet means of the vials are communicated with a means for introducing material into a region of the body. Fluid is pumped from the source through each selected vial at a sufficient rate to entrain the insoluble material in the selected vial and flush the insoluble solid material into the body. Sufficient fluid is pumped through each selected vial to flush substantially the entire content of insoluble solid material from each selected vial into the body.

In order that all of the material may be removed from the vial, a preferred vial is substantially free of edges or corners where solid materials may reside. A bottom surface of the vial declines smoothly and continuously to a lowermost region where dense insoluble material tends to accumulate. The liquid inlet means, such as a hollow needle, communicates with the interior of the vial, extending closely adjacent to the lowermost region. Liquid that is forcefully introduced through the inlet means dislodges material from the lowermost region, distributing it into the carrier liquid which then is discharged through the outlet means.

Vials containing radioactive insoluble material may be encased for distribution in radioactive shielding material and kept in radioactive shielding material during administration into a living body. Control of the liquid delivery through the vials and into the body is exercised remote from the shielded vials.

DETAILED DESCRIPTION OF CERTAIN PREFERRED EMBODIMENTS

Figure 1:
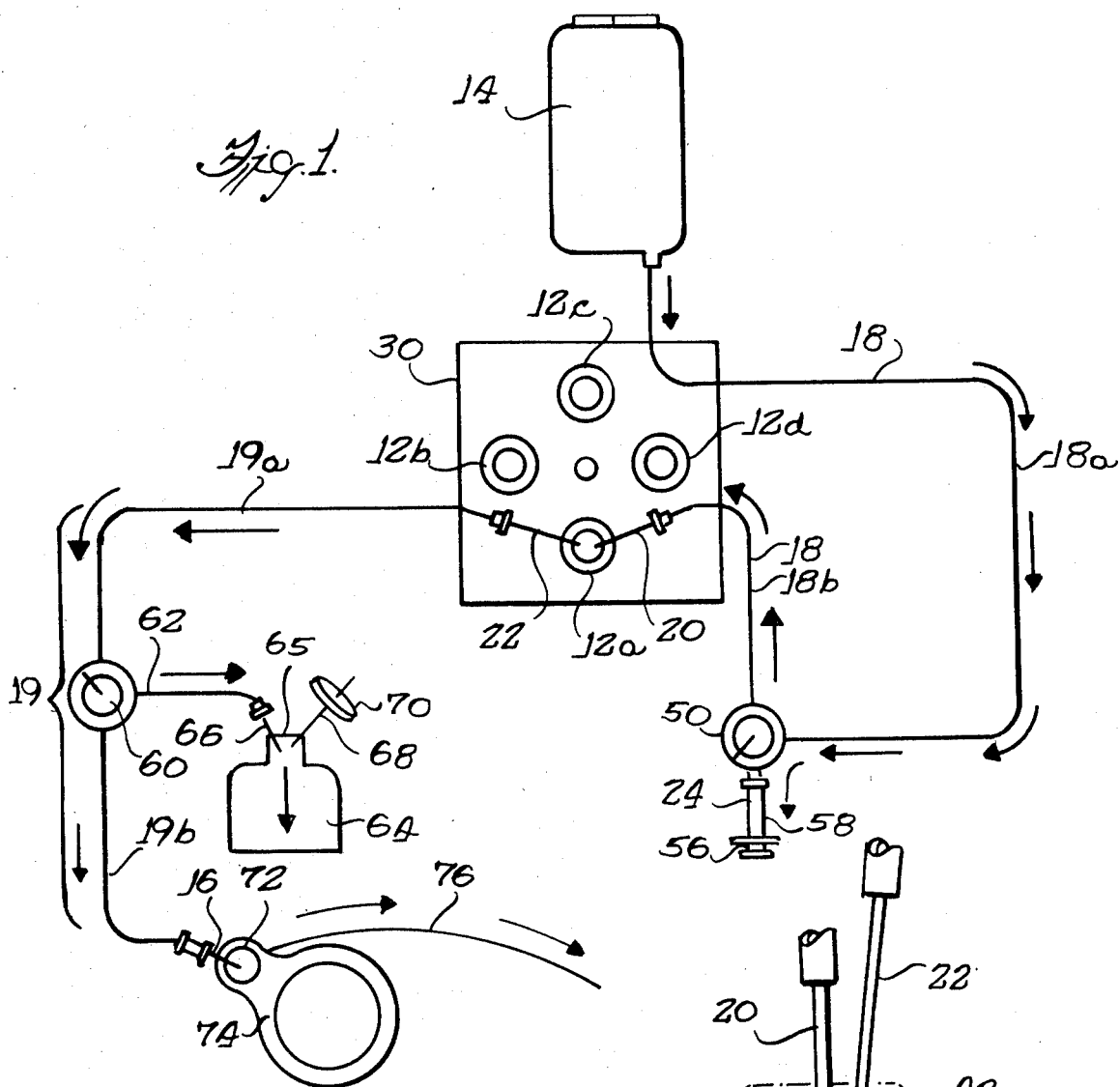
FIG. 1 is a diagrammatic illustration of a system for delivering insoluble material into an animal body.

In accordance with the present invention, an insoluble solid material 10 (FIG. 2), particularly a radioactive material, is provided for administration into a living animal body, including a human body, in a plurality of vials 12. It is intended that the entire insoluble material content of each of selected vials be delivered into the body as means of controlling dosage. A source or reservoir 14 (FIG. 1) of liquid which is compatible for internal administration is provided for carrying the insoluble material into the body, as is an access means, such as a hypodermic needle 16, for communicating with an interior region of a living body. Means, such as tubing 18, are provided for conducting liquid from the source or reservoir 14 to an inlet means, such as a hollow needle 20, extending into the selected vial or vials, and means, such as additional tubing 19, are provided for conducting liquid from an outlet means of the vial, such as another hollow needle 22, to the access means 16 communicating with the body. Means, such as a syringe 24, are provided for pumping liquid from the reservoir 14 through each selected vial 12 and into the body, the flow velocity of the pumped liquid being sufficient to entrain the insoluble material and sufficient liquid being pumped through the vial to flush substantially all of the insoluble material therefrom and into the body.

The invention provides for much greater accuracy of dosage delivery of insoluble materials 10, particularly insoluble materials which for one reason or another, e.g., high density, do not form a stable homogeneous suspension in a carrier liquid which is compatible with internal administration. The entire content of one or more selected vials 12, each with a predetermined dosage, is entrained in the carrier liquid and thereby delivered to the body. Thus, there is no concern regarding the homogeneity of insoluble material suspension.

For delivering dosages of insoluble material where the dosage per weight of material is constant, it is sufficient to provide the material in a vial that contains the entire amount necessary for a single treatment. In such cases, vials of various standard dosages can be provided so that in any administration, the entire content of any one vial may be delivered. However, where the dosage per weight of material varies with time, as is the case with radioactive isotopes incorporated in insoluble material, a single vial with a given amount will not provide a constant dosage.

To provide flexibility in delivering desired dosages of unstable or decaying material, a set of vials, each containing known amounts of the material are provided. Each vial, at the time of administration, provides either the whole dosage or a partial dosage, whereby any desired dosage can be administered by delivering the entire content(s) of one or more vial(s), the dosage being the sum of the dosages in the selected vials.

While the multi-vial system is expected to achieve substantial improvements in accuracy relative to syringe withdrawal of suspended insolubles, an immediately apparent disadvantage of a multi-vial system is the need to handle the additional vials. However, the number of vials required may be minimized by appropriate selection of vial content. Several vials could be provided, each with an identical amount of insoluble material. However, it is preferred to provide a system in which a first vial contains an amount of nmaterial and other vials have different integer multiples of the amount of material in the first vial. For example, a four vial system in which the respective vials contain 1, 2, 3 and 4 times a given amount of material may be appropriately selected to provide integer dosage increments from $1\times$ to $10\times$. In such case, if an $8\times$ dosage were desired, the combined contents of vials containing $1\times$, $3\times$ and $4\times$, would be administered.

A preferred and most efficient dosage system according to the invention includes a first vial with a lowermost amount of material and successive vials with $2^n$ times this amount where n is successive positive integers ranging from 1 to z. In such a system, any fraction having an integer numerator 1 to $2(2^z)-1$ and an integer denominator $2(2^z)-1$ may be administered by flushing the entire contents of selected vials into the body. A system where z is 3, i.e., where the vials contain $1\times$, $2\times$, $4\times$ and $8\times$ amounts can be combined in 1, 2, 3 or 4 vial arrangements to provide integer multiple increments from $1\times$ to $15\times$. For example, an $11\times$ dosage (11/15th of the total available dosage) is provided by using vials with $1\times$, $2\times$ and $8\times$ dosages. Except in the case where a $15\times$ dosage of material is required, three or less vials are required to closely approximate any desired dosage.

When using radioactive materials, the radioactivity in each vial must be known. Generally all vials of a set are filled with material, such as glass microspheres, from the same manufacture batch, in which case the radioactivity of the set of vials as a whole or of any individual vial is a measure of the radioactivity in each vial in proportion to the content by weight of each vial. The microspheres are distributed among four vials containing $1\times$, $2\times$, $4\times$, and $8\times$ amounts of microspheres.

The vials may be labeled A, B, C and D. On a given date, the total radioactivity of the four vials is measured. From this measurement and from the natural half-life of the isotope, the dosage provided by the sum of the contents of any combination of the vials can be calculated for any future date. For the convenience of the physician, the calculations are performed by the manufacturer, e.g., very simply by computer, and a chart is provided for the set of vials correlating any desired dosage with date and with the particular selection of from 1 to 4 labeled vials which most closely approximates the prescribed dosage. The table may be set up, for example, as a grid where the physician reads across for a selected dosage and down from the current date and is informed to administer selected vials, e.g., "B" plus "C". The set of vials, must of course be used before the radioactivity in the entire set drops below the dosage requirement. Usually the set is used well before the radioactivity drops this low. Therefore, in practice, the number of incremental dosage steps available from a set on a given date may be less than fifteen yet but still provide more than sufficient flexibility for a physician administering such microspheres.

Figure 2:
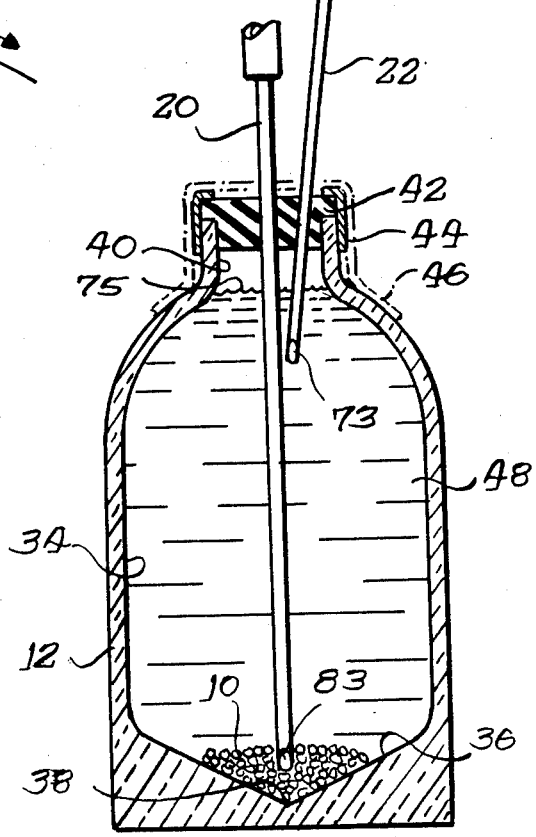
FIG. 2 is a cross-sectional view of a vial, including a self-sealing septum and a pair of hollow needles extending through the septum into the interior of the vial.

The delivery system which is represented in FIG. 1 and the vial 12 represented in greater detail in FIG. 2 represent a presently preferred embodiment of the present invention; however, it is to be appreciated that there are many variations which can be employed in such a system and that certain of the components may be substituted for or even eliminated and certain alternatives will be noted in the discussion below.

The vial 12 containing radioactive glass microspheres 10 is represented in FIG. 1 as being in a square container 30 which represents radioactive shielding. Typically, an entire set of vials 12a, 12b, 12c and 12d are shipped in such a shielded container. Most commonly, particles, such as glass microspheres, incorporate an isotope that emits exclusively beta radiation which is easily shielded with a sufficient amount of material, and therefore, the packaging box may be made of plastic. The vials 12a are held in place during administration by snugly fitting vial wells (not shown) in the plastic shielding.

Each vial 12 is selected for having an interior geometry that is unlikely to hang up the glass microspheres. To this end, a vial, as best seen in FIG. 2, is selected having an interior region that is free of edges or corners whereat the glass microspheres may tend to reside. The illustrated vial has a smooth vertical interior sidewall 34 and a concave interior bottom surface 36 that is in the shape of an inverted cone, decreasing smoothly and continuously to a lowermost point or region 38 whereat the microspheres 10 tend to accumulate because of gravity. As glass microspheres are denser than any suitable carrier solution, the microspheres accumulate along the bottom surface 36 even when the vial is filled with liquid.

An upper opening 40 of the vial 12 is sealed with a self-sealing septum 42, such as a septum formed of soft rubber, after the microspheres have been deposited in the vial and rendered sterile. A metal retaining ring 44 secures the septum 42 across the opening 40 of the vial, which is intended never to be opened. Shown in ghost is a protective cap 46 over the upper end of the vial which is removed prior to use.

Access to the interior region 48 of the vial is exclusively through the septum 42 which is punctured with two hollow needles as seen in FIG. 2. The inlet needle 20 extends through the septum 42 and substantially to the lowermost region 38 in the vial, and the outlet needle 22 opens at a position somewhat higher in the interior region of the vial.

The microspheres 10, generally occupy only a very small portion of the vial volume. Typically vials each having a capacity of about one ml. are used and the volume occupied by the microspheres in the most full vial is less than 1/10th of the volume. Preferably, the microspheres are packaged dry. However, the vials could be pre-filled with carrier solution to reduce air-evacuation time.

The liquid source or reservoir 14 is represented in FIG. 1 as a plastic bag filled with a sterile, body-compatible liquid, such as isotonic saline, lactated Ringers solution, balanced salt solution, etc. Such liquid-filled bags are conventionally used in hospitals to deliver salt solutions, nutrients and drugs to a patient. The bag is connected through the line of tubing 18 that conducts the liquid to the vial inlet needle 20. Tubing sections are typically formed of sterile plastic. Luer fittings connect the tubing sections to each other and to appropriate apparatus.

In the illustrated system, a manually operated syringe 24 provides the means of pumping liquid from the fluid reservoir 14, through the vial 12a and into the body. The pumping syringe 24 is connected to a three-way valve 50 which is openable to communicate the line segment 18a from the fluid reservoir 14 to the syringe 24 and alternately openable to communicate the syringe to the line segment 18b leading to the inlet needle 20. With the valve 50 open between the fluid reservoir 14 and the syringe 24, the piston 56 of the syringe is withdrawn from the barrel 58, drawing liquid from the reservoir into the barrel. Subsequently, with the valve open between the syringe 24 and the vial 12a, the plunging of the piston into the barrel forces the liquid through the vial and downstream thereof.

When using a manually operated syringe 24 to pump liquid through the system, the barrel 58 should neither be too large nor too small. If the interior barrel diameter is too small, it is possible to depress the piston 56 too quickly, building up excessive pressure in the vial 12 and thereby cause the septum 42 to bulge or even rupture. On the other hand too large a barrel diameter will make it difficult to depress the barrel with enough force to flush the particles from the vial 12 and into the body. It is found that when using a 5 $cm^3$ syringe, a barrel diameter of about 1 cm is appropriate.

The inlet and outlet needles 20, 22, as well as the body access needle 16, must be sufficiently large to accommodate a liquid flow of sufficient velocity to entrain the dense, insoluble microspheres 10 and also to easily accommodate passage of microspheres therethrough. Typical diameter ranges for glass microspheres are 15 to 30 microns and 30 to 50 microns. Particles of these size ranges are sufficiently small to be entrained in the blood stream of larger veins and arteries, but are larger erythrocytes (about 7 microns in their largest diameter) and lodge in the first bank of capillaries encountered. The needle and all tubing must, of course, be larger than the largest of the microspheres, and it is considered that the passageway, including the needles and tubing, must be at least 2 times the diameter of the largest particle and preferably at least 10 times the diameter of the largest particle. With microspheres between 15 and 50 microns in size, 20 gauge needles are suitable.

The outlet line 19 is connected to the outlet needle 22 for conducting liquid from the vial 12 to the bbdy access needle 16. In the simplest system, the connection between the outlet needle 22 and access needle 16 could be directly through a single length of tubing. However, in the illustrated system, an outlet line tubing segment 19*a* is connected to another three-way valve 60 which connects a tubing segment 19*b* leading from the outlet needle 22 to the body access needle 16 and, alternately, to a vent line 62.

It is necessary to evacuate air from the system before the microspheres 10 and carrier liquid are delivered to the patient. The optional vent line 62 helps to assure that radioactive microspheres, which may be inadvertently delivered during air evacuation, are contained. The vent line 62 leads to a waste vial 64. The waste vial 64 is sealed with a septum 65 through which a hollow needle 66 at the end of the vent line is inserted. A needle 68 is likewise inserted through the septum 65 and into the waste vial 64 to allow air to vent and thereby avoid pressure build-up. The vent needle 68 is preferably capped with a filter 70 that allows fluid, e.g., air and liquid, escape to avoid pressure buildup but retains all particles within the size range of the radioactive microspheres.

The body access needle 16 is shown entering a bypass port 72 of a distribution pump 74, such as that sold under the trade name Infusaid. Such pumps 74 are commonly implanted in the body of a cancer patient and used for delivering a slow, controlled dosage of chemotherapeutic agents to the afflicted organ. For use in treating a liver tumor, a catheter 76 from the pump leads into the hepatic artery. The pump is not an integral part of the delivery system of the present invention, and in fact, by inserting the needle through the bypass port 72, the microspheres 10 are carried directly through the catheter 76 and to the afflicted organ without passing through the actual pumping mechanism. However, if such a pump 74 is already implanted, the bypass port 72 provides the most convenient access to the afflicted organ. If no pump or similar access port is already implanted, surgical procedures are required to access the appropriate organ, e.g., by implanting a catheter to an artery or vein leading to that organ.

Generally, the operation of the system is as follows. Sterile tubing and sterilized components are connected together, preferably with Luer fittings, and all connected fittings are checked for tightness to insure a leak-free system. 1/32 in. tubing and a 5 cm$^3$ pumping syringe 24 may be used in the system.

The first three-way valve 50 is opened between the reservoir 14 and the pumping syringe 24, and the piston 56 is withdrawn to draw 5 cm$^3$ of liquid into the barrel 58 of the syringe.

The protective seal 46 is removed from a selected one of the vials 12a, exposing the septum 42, which is then swabbed with disinfectant, such as alcohol. The inlet or flushing needle 20 is carefully inserted through the center of the septum and pushed closely adjacent to the lowermost region 38 at the bottom surface 36 of the vial 12a. The outlet needle 22 is likewise carefully pushed through the septum, but only until it extends approximately ⅛ in. below the septum. Care is taken to assure the outlet needle 22 penetrates the septum 42; otherwise, the vial 12 can be pressurized, forcing radioactive spheres 10 back into the inlet line 18.

After all of the components are interconnected, the second three-way valve 60 is opened to establish communication between the vial 12a and the waste vial 64. The first valve 50 is switched to communicate the pumping syringe 24 and the vial 12. The piston 56 is plunged inward, forcing liquid through the inlet line 18 into the vial 12. The piston is plunged inward very slowly to minimize disturbance of the microspheres 10 and thereby avoid entrainment of microspheres into the outlet line 19. The syringe 24 is discharged slowly until the vial 12 and the lines 18, 19a, 62 are filled with liquid, as indicated by liquid discharging from needle 66.

At this time, the outlet needle 22 is pushed further into the microsphere-containing vial, e.g., about another ⅛ inch, to ensure that the tip 73 of the outlet needle 22 is below the surface 75 of the water and thereby prevent air trapped at the upper end of the vial 12 from being entrained into the liquid stream flowing to the body.

Next, the second three-way valve 60 is actuated to communicate the vial 12a with the body access needle 16. A small void volume remains in the tubing segment 19b leading to this needle and in the needle itself, and liquid is pumped in very slowly until a first drop is discharged from the body access needle 16. Then the body access needle 16 is inserted in communication with an interior region of the body, e.g., in communication with the hepatic artery through the bypass port 72 of the implanted pump 74.

The procedure for flushing the microspheres from their vial 12 is substantially the same as the procedure for air evacuation, except that liquid is pumped through the system at a rate sufficient to entrain the microspheres. As in air evacuation, the first three-way valve 50 is opened to communicate the fluid source 14 with the syringe, the piston is withdrawn, the three-way valve is actuated to communicate the syringe with the vial 12 and the piston is plunged inward, this time at a much higher rate. Using 20 gauge needles and 1/32 inch tubing, depressing the plunger of a 5 cm$^3$ syringe over a period of 5 seconds is sufficient to entrain microspheres into the liquid flowing through the outlet line 19.

When liquid is pumped through the system at a sufficient rate, entry of liquid through the tip 83 of the inlet needle 20 creates a turbulence in the liquid in the vial 12 sufficient to create an unstable suspension of microspheres in the liquid within the vial, and the liquid leaving the vial carries the entrained microspheres downstream. With glass microspheres having a density just over 3 g/cm$^3$ and diameters of up to 50 microns in diameter, there is no difficulty in flushing substantially all of the microspheres from the vial and into the body. If denser microspheres are used, e.g., microspheres formed of metals containing radioactive isotopes, it may be necessary to use microspheres toward the low end of the permissible size range, e.g., 15–30 microns, and/or to increase the flow rate through the system.

Using a vial 0.9 cm$^3$ in volume and 2 rinses, each delivered at 5 cm$^3$ per 5 sec discharges, 93% of 30–50 micron diameter microspheres are flushed from the vial. Three rinses deliver 96% of the microspheres, 4 rinses 98% and 5 rinses 99%. These percentages were measured experimentally by determining the weight of microspheres flushed out of catheter 76. These percentages can be expected to change somewhat with particular equipment. As it will generally be impractical to measure residual activity of the vials in the hospital setting, the manufacturer will generally prescribe that a certain volume of liquid be discharged through the vial to assure that substantially all, e.g., over 95%, of the microspheres are discharged.

When more than one of the vials are needed to deliver a prescribed dosage, the procedures are repeated, first withdrawing the inlet and outlet needles from the emptied vial and inserting them into the fresh vial. The air-evacuation is repeated, and then the microspheres are flushed through the system as before.

After the contents of the selected vials of the set are flushed into the patient, the needle 16 connected with the patient is withdrawn. Then the vial 12 is replaced with a water-containing vial, and a low volume of water is flushed through the outlet and vent lines to the waste vial to reduce any radioactivity that might reside in the apparatus.

Also, a small volume of saline may be separately injected into the patient to flush any activity remaining in the bypass port 72 of the pump 74 and/or the catheter system 76.

Operation of the system described above is entirely manual. It may, however, be desirable to install more complex components in a delivery system. For example, a mechanical device may be used to operate the syringe to provide a better control of liquid flow rates, slowly at first for evacuating air from the system and then with sufficient velocity for flushing microspheres through the system. To avoid the need to continuously actuate a three-way valve associated with the syringe, syringes with one-direction valving systems, such as those used in automatic pipetting systems, may be used. The need for a syringe may be avoided entirely using mechanical pumps, such as peristaltic pumps with adjustable flow rates.

A major advantage of the system of the present invention is that it provides for accurate control of dosage delivery for insoluble particles, such as radioactive microspheres. Accuracy is assured by a system that relies upon delivery of the entire insoluble content from a vial. By avoiding the need to rely on homogeneity of particle suspension, as is the case with prior art systems in which a volume of suspended particles are withdrawn by syringe, reliability of dosage measurement is assured. The multi-vial system is particularly important for delivering a specific dose of radioactive material where the radioactivity is decreasing continuously so that the radioactive content of each vial is meaningful only as a function of time from any particular direct measurement of radioactivity.

Another very important advantage of the invention is the protection it affords the physician from radiation. The vials 12 containing the radioactive material can be packaged in shielding material and delivered directly from the vials within the shielding packaging to the patient. There is no need for the physician to hold a syringe full of radioactive material and slowly administer it into the patient. Operation of the syringe 24 or other pumping means by which the physician flushes the material into the patient is entirely remote from the vial itself, and the physician may be fully shielded from the radioactive emissions of the material within the vials. Any or all parts of the tubing may be shielded from the physician. For example, a clear plastic shield (not shown) may be placed between the physician and the delivery system with only the pumping syringe 24 extending through a port in the shield. In the case of beta radiation, shielding may be provided by a wide variety of materials, including plastic.

Although there is some exposure to radiation when the needles are inserted into the vials, this operation requires very little time, and exposure is minimal. Furthermore, as this is not a particularly delicate operation, it is easier to provide adequate shielding for inserting needles into a vial than it is to provide adequate shielding for a syringe which a physician must carefully manipulate.

The system described above has advantages in that it uses simple components that are very simple to assemble. It is contemplated that more sophisticated apparatus could be provided in accordance with the invention. For example, the above-described system contemplates individual vials which are individually connected to the system and individually flushed. As an alternative, several vials could be preconnected via a multiply valved manifold, allowing selected vials to be successively, or even simultaneously, flushed by manipulation of valves of the manifold. Such a system would have the advantage that the valves and connecting fittings could be provided extending from the shielding packaging material so that connecting the components of the system would entail substantially no exposure to radiation. In such case, it would be desirable to provide clear plastic shielding material (if beta radiation were used) so that proper flow through the individual vials could be externally observed.

While the invention has been described in terms of certain preferred embodiments, modifications obvious to one with ordinary skill in the art may be made without departing from the scope of the present invention.

Various features of the invention are set forth in the following claims.

What is claimed is:

1. A vial assembly for use in a system for delivering an amount of glass microspheres containing a radioactive isotope entrained in a liquid having a lower density than said microspheres into the body of a living mammal, said vial assembly comprising:
   a vial having a bottom wall and a sidewall defining an interior which is substantially symmetrical about a vertical axis, an open mouth at the top of said vial, said bottom wall having a surface that is substantially in the shape of an inverted cone to define a depression for receiving a supply of said microspheres and said sidewall having a substantially smooth inner surface;
   a supply of said microspheres disposed in said depression; and
   a septum closing the mouth of said vial.

2. A system for delivering an amount of glass microspheres containing a radioactive isotope entrained in a liquid having a lower density than said microspheres into the body of a living mammal, said system comprising:
   a vial defining an interior which is substantially symmetrical about a vertical axis and including a bottom wall and a sidewall defining said interior, said vial further having an open mouth at the top of the vial, said bottom wall having a surface having a depression for receiving a supply of said microspheres, said sidewall having a substantially smooth inner surface;
   a supply of microspheres containing a radioactive isotope disposed in said depression;
   a septum closing the mouth of said vial;
   a supply of liquid;
   an inlet needle passing though said septum, directed at said supply of micropsheres and having a distal end terminating adjacent said bottom wall surface;
   a pump and associated tubing interconnecting said liquid supply and said inlet needle;
   an outlet needle passing through said septum and having a distal end terminating in said interior above said supply of microspheres; whereby upon connection of the outlet needle to a living body, operation of said pump causes a jet of said liquid to be directed at said supply of microspheres causing sufficient agitation to entrain said microspheres in the quantity of liquid in said interior and furthermore to force microspheres entrained in said liquid through said outlet needle.

3. A system as set forth in claim 2 wherein said inlet needle extends substantially along the axis of said interior and the distal end of said inlet needle is disposed in said supply of microspheres.

4. A system as set forth in claim 2 wherein said supply of microspheres is disposed below said sidewall.

5. A system as set forth in claim 2 wherein said distal end of said outlet needle is disposed adjacent the axis of said interior.

6. A system as set forth in claim 2 wherein said supply of microspheres occupies less than 1/10th of the volume of said interior.

7. A system as set forth in claim 2 wherein said microspheres each have a density of about 3 g/cm$^3$.

8. A system as set forth in claim 2 wherein said liquid is isotonic saline.

* * * * *

UNITED STATES PATENT AND TRADEMARK OFFICE
CERTIFICATE OF CORRECTION

PATENT NO. : 4,745,907
DATED : May 24, 1988
INVENTOR(S) : Russell, Jr. et al.

It is certified that error appears in the above-identified patent and that said Letters Patent is hereby corrected as shown below:

Face, Inventor, change "Russel" to --Russell--.

References under "Riddell" change class "64" to --604--.

Column 3, line 4, change ":" to --;--.

Column 4, line 6, change "nmaterial" to --material--.

Column 6, line 29, after "larger" insert --than--.

Column 6, line 40, change "bbdy" to --body--.

Column 7, line 3, change "in.tegral" to --integral--.

Signed and Sealed this

Eleventh Day of October, 1988

Attest:

DONALD J. QUIGG

*Attesting Officer*          *Commissioner of Patents and Trademarks*